US012624017B2

(12) United States Patent
Ge et al.

(10) Patent No.: US 12,624,017 B2
(45) Date of Patent: May 12, 2026

(54) SALT FORM OF ISOQUINOLINONE TYPE COMPOUND AS ROCK INHIBITOR AND PREPARATION METHOD THEREFOR

(71) Applicants: GUANGZHOU OCUSUN OPHTHALMIC BIOTECHNOLOGY CO., LTD., Guangzhou (CN); OCUSUN OPHTHALMIC PHARMACEUTICAL (GUANGZHOU) CO., LTD., Guangzhou (CN)

(72) Inventors: Jian Ge, Guangzhou (CN); Yandong Wang, Guangzhou (CN); Yizhi Liu, Guangzhou (CN); Lingyun Wu, Shanghai (CN); Xu You, Shanghai (CN); Zheming Xiao, Shanghai (CN); Shuhui Chen, Shanghai (CN)

(73) Assignees: GUANGZHOU OCUSUN OPHTHALMIC BIOTECHNOLOGY CO., LTD., Guangzhou (CN); OCUSUN OPHTHALMIC PHARMACEUTICAL (GUANGZHOU) CO., LTD., Guangzhou (CN)

( * ) Notice: Subject to any disclaimer, the term of this patent is extended or adjusted under 35 U.S.C. 154(b) by 446 days.

(21) Appl. No.: 18/338,355

(22) Filed: Jun. 21, 2023

(65) Prior Publication Data

US 2023/0331696 A1 Oct. 19, 2023

Related U.S. Application Data

(63) Continuation of application No. PCT/CN2021/140206, filed on Dec. 21, 2021.

(30) Foreign Application Priority Data

Dec. 21, 2020 (CN) ........................ 202011521011.6

(51) Int. Cl.
*C07D 401/12* (2006.01)

(52) U.S. Cl.
CPC ........ *C07D 401/12* (2013.01); *C07B 2200/11* (2013.01)

(58) Field of Classification Search
CPC .................................................... C07D 401/12
(Continued)

(56) References Cited

U.S. PATENT DOCUMENTS 12,459,918 B2 * 11/2025 Liu et al. ............. C07D 401/12
2023/0024516 A1 1/2023 Liu et al.

FOREIGN PATENT DOCUMENTS

CN 101068806 A 11/2007
CN 101622243 A 1/2010
(Continued)

OTHER PUBLICATIONS

Gould PL. Salt selection for basic drugs. International journal of pharmaceutics. Nov. 1, 1986;33(1-3):201-17. (Year: 1986).*
(Continued)

*Primary Examiner* — Jeffrey S Lundgren
*Assistant Examiner* — Heather Dahlin

(57) ABSTRACT

Disclosed is a salt form of an isoquinolinone type compound as a ROCK protein kinase inhibitor and a preparation method therefor, and use of the salt form in the preparation of a medicament for treating glaucoma or ocular hypertension is further included.

(Continued)

(II)

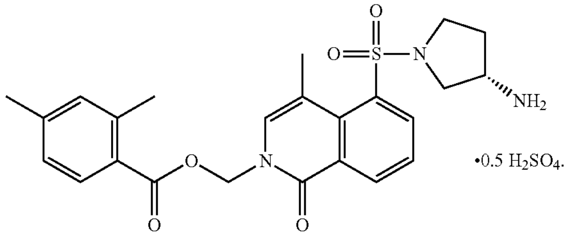

•0.5 $H_2SO_4$.

16 Claims, 4 Drawing Sheets

(58) Field of Classification Search
USPC .......................................................... 514/307
See application file for complete search history.

(56) References Cited

FOREIGN PATENT DOCUMENTS

| | | | |
|---|---|---|---|
| CN | 101622243 | B | 12/2013 |
| CN | 105085478 | A | 11/2015 |
| EA | 11283 | B1 | 2/2009 |
| EP | 2130828 | A1 | 12/2009 |
| JP | 2007026664 | A | 2/2007 |
| JP | 2008105442 | A | 5/2008 |
| JP | 2017513919 | A | 6/2017 |
| JP | 2022538086 | A | 8/2022 |
| RU | 2376300 | C1 | 12/2009 |
| WO | 2006057397 | A1 | 6/2006 |
| WO | 2007026664 | A1 | 3/2007 |
| WO | 2020253882 | A1 | 12/2020 |
| WO | 2022135421 | A1 | 6/2022 |

OTHER PUBLICATIONS

Bhattacharya S, Brittain HG, Suryanarayanan R. Thermoanalytical and crystallographic methods. InPolymorphism in pharmaceutical solids Nov. 12, 2018 (pp. 330-358). CRC Press. (Year: 2018).*
International Search Report dated Mar. 10, 2022 in International Application No. PCT/CN2021/140206.English translation attached.
Extended European Search Report from corresponding European Application No. EP21909417.4, dated May 27, 2024.
First Office Action dated Jul. 2, 2024 received in corresponding patent family application No. JP2023-561419. English translation attached.
First Office Action dated Aug. 1, 2024 received in corresponding patent family application No. CA3,202,841.
First Office Action dated Jan. 24, 2024 received in patent family application No. RU2023118927. English translation attached.
First Office Action dated Nov. 24, 2023 received in corresponding patent family application No. AU2021408195.
First Office Action dated Oct. 31, 2025 received in corresponding patent family application No. IN202327049061. English translation attached.
First Office Action dated Sep. 22, 2025 received in corresponding patent family application No. KR1020237025004. English translation attached.

* cited by examiner

SALT FORM OF ISOQUINOLINONE TYPE COMPOUND AS ROCK INHIBITOR AND PREPARATION METHOD THEREFOR

CROSS-REFERENCE TO RELATED APPLICATIONS

This application is a continuation of International Application No. PCT/CN2021/140206, filed on Dec. 21, 2021, which claims priority to Chinese Application No. 202011521011.6, filed on Dec. 21, 2020. The disclosures of the aforementioned applications are hereby incorporated by reference in their entireties.

TECHNICAL FIELD

The present disclosure relates to a salt form of an isoquinolinone type compound as a ROCK inhibitor and a preparation method therefor, and also includes a use of the salt form in the preparation of a medicament for treating glaucoma or ocular hypertension.

BACKGROUND

Rho-associated kinase (ROCK), a serine/threonine protein kinase, is a downstream effector molecule of RHO and widely expressed in the human body. ROCK is involved in the regulation of myosin light chain (MLC). It is suitable for the treatment of vasodilation. ROCK can also act on trabecular outflow tract cells to decrease the resistance to the outflow of aqueous by relax trabecular cells. Recent research shows that ROCK inhibitors can also promote the repair of corneal endothelial cells and prevent fibrosis, which has great application prospects.

Isoquinoline sulfonamide compounds are an important class of ROCK inhibitors. Fasudil and K-115 (WO2006057397A1), which have been launched at present, are both isoquinoline sulfonamide compounds. Fasudil, as a novel drug with extensive pharmacological effects, is a RHO kinase inhibitor, which expands blood vessels by increasing the activity of myosin light chain phosphatase, reduces the tension of endothelial cells, improves the microcirculation of brain tissue without producing or aggravating cerebral steal. And at the same time, it can antagonize inflammatory factors, protect nerves, resist apoptosis, and promote nerve regeneration. However, the approval of K-115 has very wide potential applications, including glaucoma, ocular hypertension, diabetic retinal damage complications, age-related macular degeneration, corneal damage, recovery after cataract and glaucoma surgery, etc., and may be further expanded to systematic drugs.

WO2007026664A1 reported a series of compounds with ROCK inhibitory effects, such as control compound 2, which have good enzymatic activity, but need to be improved in terms of membrane permeability, pharmacokinetics, druggability and other aspects. The present disclosure reports a class of similar compounds that have been structurally modified and have significantly improved properties in this regard

K-115

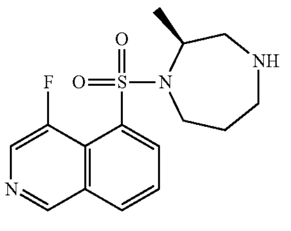

-continued

Control compound 2

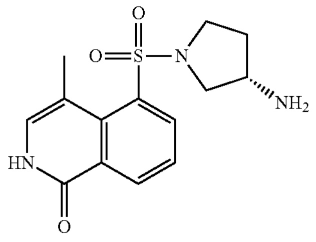

SUMMARY

The present disclosure provides a compound of formula (II), (II)

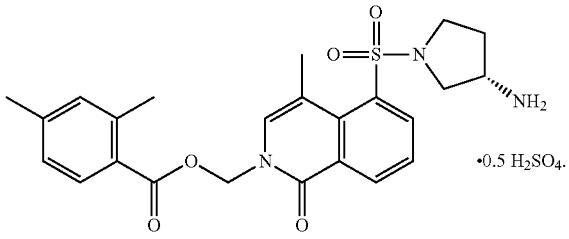

•0.5 $H_2SO_4$.

The present disclosure further provides a crystal form A of the compound of formula (II), with an X-ray powder diffraction pattern having characteristic diffraction peaks at the following angles of 2θ: 6.33±0.20°, 10.62±0.20°, and 13.11±4.20°, (II)

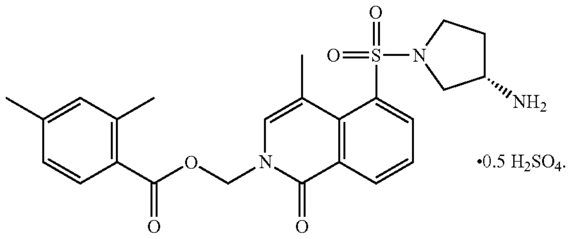

•0.5 $H_2SO_4$.

In some embodiments of the present disclosure, the X-ray powder diffraction pattern of the crystal form A has characteristic diffraction peaks at the following angles of 2θ: 3.30±0.20°, 6.33±0.20°, 6.55±0.20°, 10.62±0.20°, 12.57±0.20°, and 13.11±0.20°.

In some embodiments of the present disclosure, the X-ray powder diffraction pattern of the crystal form A has characteristic diffraction peaks at the following angles of 2θ: 3.30±0.20°, 6.33±0.20°, 10.62±0.20°, 12.57±0.20°, 13.11±0.20°, 17.85±0.20°, 18.51±0.20°, and 20.99±0.20°.

In some embodiments of the present disclosure, the X-ray powder diffraction pattern of the crystal form A has characteristic diffraction peaks at the following angles of 2θ: 3.30±0.20°, 6.33±0.20°, 6.55±0.20°, 10.62±0.20°, 12.57±0.20°, 13.11±0.20°, 14.20±0.20°, 16.37±0.20°, 17.85±0.20°, 18.51±0.20°, 19.56±0.20°, 20.99±0.20°, 25.53±0.20°, and 26.35±0.20°.

In some embodiments of the present disclosure, the X-ray powder diffraction pattern of the crystal form A is substantially as shown in FIG. 1.

In some embodiments of the present disclosure, the X-ray powder diffraction pattern analysis data of the crystal form A is as shown in Table 1.

TABLE 1

The X-ray powder diffraction pattern analysis data of the crystal form A of the compound of formula (II)

| No. | angles of 2θ(°) | Interplanar distance (Å) | Intensity (count) | Relative intensity (%) |
|---|---|---|---|---|
| 1 | 3.30 | 26.76 | 348.60 | 43.99 |
| 2 | 6.33 | 13.95 | 779.58 | 98.38 |
| 3 | 6.55 | 13.50 | 475.77 | 60.04 |
| 4 | 10.62 | 8.33 | 562.38 | 70.97 |
| 5 | 12.57 | 7.04 | 226.50 | 28.58 |
| 6 | 13.11 | 6.76 | 792.44 | 100.00 |
| 7 | 14.20 | 6.24 | 122.94 | 15.51 |
| 8 | 16.37 | 5.42 | 178.19 | 22.49 |
| 9 | 17.85 | 4.97 | 228.61 | 28.85 |
| 10 | 18.51 | 4.79 | 198.30 | 25.02 |
| 11 | 19.56 | 4.54 | 192.79 | 24.33 |
| 12 | 20.99 | 4.23 | 232.26 | 29.31 |
| 13 | 25.53 | 3.49 | 170.02 | 21.46 |
| 14 | 26.35 | 3.38 | 149.03 | 18.81 |

In some embodiments of the present disclosure, the X-ray powder diffraction pattern of the crystal form A is obtained using a Cu-Kα radiation source.

In some embodiments of the present disclosure, a differential scanning calorimetry curve of the crystal form A has an endothermic peak with an onset at 235.9±3.0° C.

In some embodiments of the present disclosure, the differential scanning calorimetry curve of the crystal form A is substantially as shown in FIG. 2.

In some embodiments of the present disclosure, a thermogravimetric analysis curve of the crystal form A shows a weight loss up to 7.70% at 160.0±3.0° C.

In some embodiments of the present disclosure, the thermogravimetric analysis curve of the crystal form A is substantially as shown in FIG. 3.

The present disclosure further provides a crystal form B of a compound of formula (II), with an X-ray powder diffraction pattern having characteristic diffraction peaks at the following angles of 2θ: 16.48±0.20°, 16.95±0.20°, and 21.87±0.20°, (II)

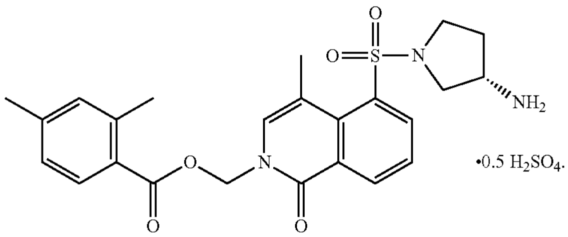

•0.5 $H_2SO_4$.

The present disclosure further provides a crystal form B of a compound of formula (II), with an X-ray powder diffraction pattern having characteristic diffraction peaks at the following angles of 2θ: 9.69±0.20°, 12.12±0.20°, and 21.87±0.20°, (II)

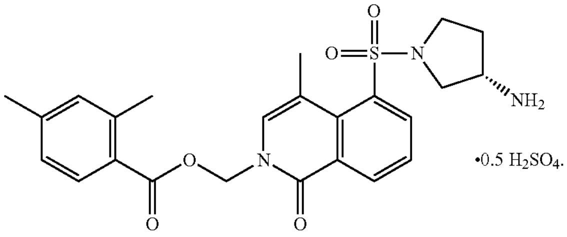

•0.5 $H_2SO_4$.

In some embodiments of the present disclosure, the X-ray powder diffraction pattern of the crystal form B has characteristic diffraction peaks at the following angles of 2θ: 12.12±0.20°, 16.48±0.20°, 16.95±0.20°, 17.94±0.20°, and 21.87±0.20°.

In some embodiments of the present disclosure, the X-ray powder diffraction pattern of the crystal form B has characteristic diffraction peaks at the following angles of 2θ: 9.69±0.20°, 12.12±0.20°, 16.48±0.20°, 16.95±0.20°, and 21.87±0.20°.

In some embodiments of the present disclosure, the X-ray powder diffraction pattern of the crystal form B has characteristic diffraction peaks at the following angles of 2θ: 9.69±0.20°, 12.12±0.20°, 16.48±0.20°, 16.95±0.20°, 17.94±0.20°, 19.23±0.20°, 20.37±0.20°, and 21.87±0.20°.

The present disclosure provides a crystal form B of a compound of formula (II), with a X-ray powder diffraction pattern having characteristic diffraction peaks at the following angles of 2θ: 16.48±0.20°, 16.95±0.20°, and/or 21.87±0.20°, and/or 12.12±0.20°, and/or 17.94±0.20°, and/or 9.69±0.20°, and/or 20.37±0.20°, and/or 21.87±0.20°, and/or 4.80±0.20°, and/or 14.61±0.20°, and/or 19.23±0.20°, and/or 27.53±0.20°, and/or 28.72±0.20°, and/or 33.61±0.20°.

In some embodiments of the present disclosure, the X-ray powder diffraction pattern of the crystal form B has characteristic diffraction peaks at the following angles of 2θ: 4.80±0.20°, 9.69±0.20°, 12.12±0.20°, 14.61±0.20°, 16.48±0.20°, 16.95±0.20°, 17.94±0.20°, 19.23±0.20°, 20.37±0.20°, 21.87±0.20°, 27.53±0.20°, 28.72±0.20°, and 33.61±0.20°.

In some embodiments of the present disclosure, the X-ray powder diffraction pattern of the crystal form B has characteristic diffraction peaks at the following angles of 2θ: 4.80±0.20°, 9.69±0.20°, 12.12±0.20°, 16.48±0.20°, 16.95±0.20°, 17.94±0.20°, 19.23±0.20°, 20.37±0.20°, and 21.87±0.20°.

In some embodiments of the present disclosure, the X-ray powder diffraction pattern of the crystal form B is substantially as shown in FIG. 4.

In some embodiments of the present disclosure, the X-ray powder diffraction pattern analysis data of the crystal form B is shown in Table 2.

TABLE 2

The X-ray powder diffraction pattern analysis data of the crystal form B of the compound of formula (II)

| No. | angles of 2θ(°) | Interplanar distance (Å) | Intensity (count) | Relative intensity (%) |
|---|---|---|---|---|
| 1 | 4.80 | 18.4 | 192.63 | 11.68 |
| 2 | 9.69 | 9.13 | 490.29 | 29.73 |

TABLE 2-continued

The X-ray powder diffraction pattern analysis data of the crystal form B of the compound of formula (II)

| No. | angles of 2θ(°) | Interplanar distance (Å) | Intensity (count) | Relative intensity (%) |
|---|---|---|---|---|
| 3 | 12.12 | 7.30 | 499.73 | 30.30 |
| 4 | 14.61 | 6.06 | 47.37 | 2.87 |
| 5 | 16.48 | 5.38 | 1649.30 | 100.00 |
| 6 | 16.95 | 5.23 | 1212.17 | 73.50 |
| 7 | 17.94 | 4.94 | 228.71 | 13.87 |
| 8 | 19.23 | 4.62 | 250.69 | 15.20 |
| 9 | 20.37 | 4.36 | 319.43 | 19.37 |
| 10 | 21.87 | 4.06 | 983.84 | 59.65 |
| 11 | 27.53 | 3.24 | 41.99 | 2.55 |
| 12 | 28.72 | 3.11 | 159.82 | 9.69 |
| 13 | 33.61 | 2.67 | 55.60 | 3.37 |

In some embodiments of the present disclosure, the X-ray powder diffraction pattern of the crystal form B is obtained using a Cu-Kα radiation source.

In some embodiments of the present disclosure, a differential scanning calorimetry curve of the crystal form B has an endothermic peak with an onset at 239.5±3.0° C.

In some embodiments of the present disclosure, the differential scanning calorimetry curve of the crystal form B is substantially as shown in FIG. 5.

In some embodiments of the present disclosure, a thermogravimetric analysis curve of the crystal form B shows a weight loss up to 1.30% at 200.0±3.0° C.

In some embodiments of the present disclosure, the thermogravimetric analysis curve of the crystal form B is substantially as shown in FIG. 6.

The present disclosure further provides a preparation method for a crystal form B of a compound of formula (II). The preparation method includes:

(a) adding a crystal form A of the compound of formula (II) into a solvent to form a suspension; and (b) stirring the suspension at 50° C. for 3 h, filtering and drying.

The said solvent is selected from the group consisting of isopropanol, tetrahydrofuran, acetonitrile, 2-butanone, and ethyl acetate.

In some embodiments of the present disclosure, applications of the compound of formula (II), the crystal form A, and the crystal form B in the preparation of ROCK inhibitor related drugs are provided.

In some embodiments of the present disclosure, applications of the compound of formula (II), the crystal form A, and the crystal form B in the preparation of a medicament for treating glaucoma or ocular hypertension.

Technical Effects

The compound of formula (I) significantly increases the exposure amount of an active drug, and significantly increases the peak concentration of drug in plasma Cmax and the action time. In an acute intraocular hypertension model, the compound of formula (I) demonstrates good ocular pressure reduction effects at different test doses, and has a certain dose correlation, and the intraocular pressure reduction amplitude and the action duration are both better than those of K-115. The compound of formula (I) has excellent efficacy (highest intraocular pressure reduction effect and longest action time). The compound of formula (I) has high system safety.

Definition and Explanation

Unless otherwise indicated, the following terms and phrases used herein are intended to have the following meanings. A particular phrase or term should not be considered indefinite or unclear in the absence of a special definition, but should be understood in accordance with its ordinary meaning. When a trade name appears herein, it is intended to refer to a product or its active ingredient corresponding to the trade name.

An intermediate compound of the present disclosure may be prepared by a variety of synthetic methods well known to those skilled in the art, including specific embodiments listed below, embodiments formed by combining them with other chemical synthesis methods, and equivalent substitute methods well known to those skilled in the art. Preferred embodiments include, but are not limited to, examples of the present disclosure.

Chemical reactions in the specific embodiments of the present disclosure are accomplished in suitable solvents, and the solvents must be suitable for chemical changes of the present disclosure, as well as reagents and materials required therefor. In order to obtain the compound of the present disclosure, it is sometimes necessary for those skilled in the art to modify or select synthesis steps or reaction procedures on the basis of existing embodiments.

The structure of the compound of the present disclosure may be confirmed by conventional methods well known to those skilled in the art; and if an absolute configuration of the compound is involved in the present disclosure, the absolute configuration may be verified by conventional technical means in the art. For example, a single crystal X-ray diffraction (SXRD) method is used, in which diffraction intensity data is collected for a cultivated single crystal using a Bruker D8 venture diffractometer with CuKα radiation as the light source, and a scanning mode: φ/scanning; and after collecting the relevant data, a direct method (Shelxs97) is used to analyze a crystal structure, which can verify the absolute configuration.

The present disclosure is described specifically below by means of examples, but these examples are not intended for any limitations on the present disclosure.

All solvents used in the present disclosure are commercially available and can be used without further purification.

The present disclosure uses the following abbreviations: r.t. represents room temperature; THF represents tetrahydrofuran; NMP represents N-methyl-2-pyrrolidone; $MeSO_3H$ represents methanesulfonic acid; DME represents ethylene glycol dimethyl ether; DCM represents dichloromethane; Xphos represents 2-dicyclohexylphosphino-2°,4,'6'-triisopropylbiphenyl; EtOAc represents ethyl acetate; MeOH represents methanol; acetone represents 2-propanone; 2-Me-THF represents 2-methyltetrahydrofuran; and IPA represents isopropanol.

The compounds are named according to conventional naming principles in the art or using ChemDraw® software, and commercially available compounds are used under supplier catalog names.

X-Ray Powder Diffraction (XRPD) Method

Instrument model: PANalytical X'pert$^3$ X-ray powder diffractometer

Test method: approximately 10 mg of sample for XRPD detection.

The detailed XRPD parameters are as follows:

a radiation source: Cu, Kα1=1.540598 Å; Cu, Kα2=1.544426 Å tube voltage: 40 kV; tube current: 40 mA scanning range: 3-40 deg
step width angle: 0.0263 deg
step length: 46.665 seconds.

Differential Scanning Calorimetry (DSC) Method

Instrument model: TA2500 differential scanning calorimeter

Test method: a sample (about 1 to 5 mg) was placed in a DSC aluminum disc for testing, the aluminum disc being covered with a cover and having no perforated holes; and the sample was heated from 25° C. (room temperature) at a heating rate of 10° C./min under 50 mL/min $N_2$ till the sample decomposed.

Thermal Gravimetric Analysis (TGA) Method

Instrument model: TAQ5000 thermal gravimetric analyzer

Test method: a sample (about 1 to 5 mg) was placed in a TGA aluminum disc for testing, the aluminum disc being uncovered; and the sample was heated from room temperature to 350° C. at a heating rate of 10° C./min under 10 to 25 mL/min $N_2$.

Dynamic Vapor Sorption (DVS) Method

Instrument model: SMS DVS intrinsic dynamic vapor sorption instrument

A dynamic water sorption experiment consists of adsorption and desorption. It is generally believed that at a set relative humidity, the adsorption or desorption of the sample to moisture at this relative humidity is considered to have reached equilibrium when the sample weight reaches dm/dt≤0.01%.

Sample testing temperature: T=25° C.
Equilibrium time: dm/dt: 0.01%/min
Relative humidity variation range: 0%-95%-0%; RH (%)
Test humidity change at each step: 5%
The evaluation of hygroscopicity is classified as follows:

| Classification of hygroscopicity | ΔW % |
|---|---|
| Deliquescent | Enough moisture adsorbed to form a liquid |
| Very hygroscopic | ΔW % ≥ 15% |
| Hygroscopic | 15% > ΔW % ≥ 2% |
| Slightly hygroscopic | 2% > ΔW % ≥ 0.2% |
| Non-hygroscopic | ΔW % < 0.2% |

Note:
ΔW% indicates the hygroscopic weight gain of the test sample at 25 ± 1° C. and 80 ± 2% RH.

DESCRIPTION OF EMBODIMENTS

Figure 1:
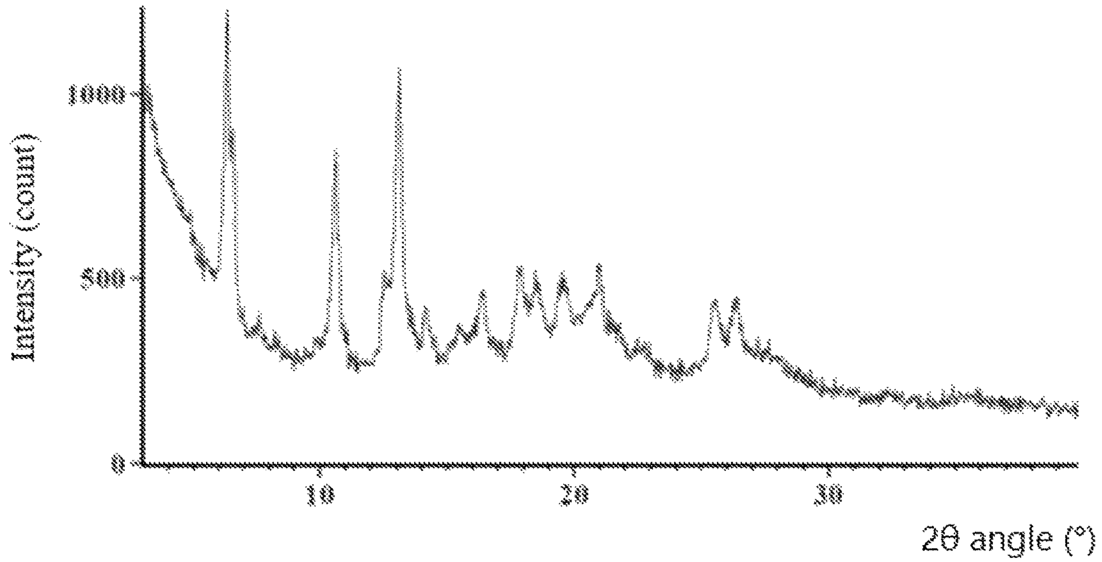
FIG. 1 is an XRPD pattern of a crystal form A of a compound of formula (II) under Cu-Kα radiation.

In order to better understand the content of the present disclosure, a further description is made in conjunction with specific examples, which should not be construed as limitations on the content of the present disclosure.

Intermediate 1-4

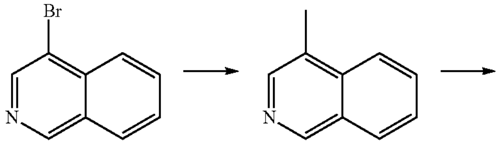

1-4a 1-4b

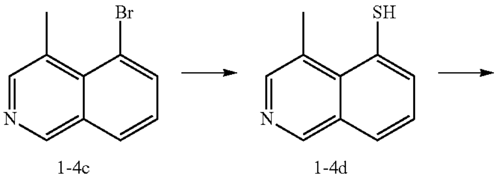

1-4c 1-4d

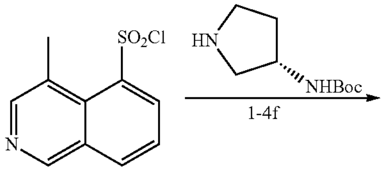

1-4e

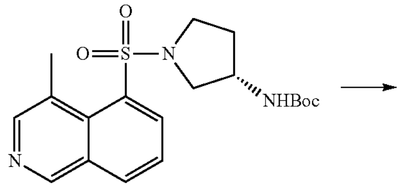

1-4g

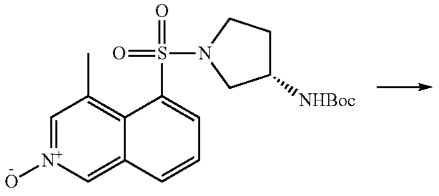

1-4h

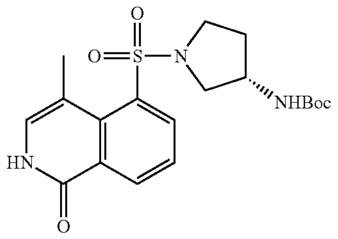

1-4

Step 1:

With an internal temperature controlled at 25 to 35° C., toluene (24 L), compound 1-4a (4000 g), sodium carbonate (6120 g), methylboronic acid (3465 g), 2-dicyclohexylphosphino-2',6'-dimethoxybiphenyl (98.66 g), and tris(dibenzylideneacetone)dipalladium (88.03 g) were added sequentially to a reactor under stirring, the reactor was subjected to nitrogen displacement for three times, the internal temperature was raised to 90° C., and the mixture was stirred at 90 to 100° C. for 13 h. Water (4 L) was added to the reactor to dissolve the solid, the reaction solution was cooled to room temperature and filtered with diatomite, and the filter cake was washed with methyl tert-butyl ether (4 L). The washing solution and the filtrate were combined, adjusted with concentrated hydrochloric acid (8 L) to pH=3, and standing liquid for stratification. The aqueous phase was extracted with methyl tert-butyl ether (5 L), and the aqueous phase was adjusted with a sodium hydroxide aqueous solution to pH=9, and extracted twice with ethyl acetate (12 L); and the combined organic phase was concentrated under vacuum until the weight no longer decreased to obtain compound 1-4b.

MS-ESI (M+H)': calculated 144, and measured 144.

Step 2:

With the temperature in a reactor (50 L) controlled to below 30° C., concentrated sulfuric acid (13.36 L) was slowly added to the reactor. The temperature in the reactor was controlled to be lower than 50° C., at which compound 1-4b (2500 g) was slowly added to the reactor with a constant-pressure dropping funnel. The temperature in the reactor was controlled at −10 to 0° C., at which N-bromosuccinimide (3070.25 g) was slowly added to the reactor in batches, and the reaction solution was stirred for 13 h at −10 to 8° C. The internal temperature was controlled to below 50° C., and the reaction solution was slowly poured into ice water (8 L). The internal temperature was controlled to below 50° C., and the reaction solution was adjusted to pH=9 by slowly adding a sodium hydroxide aqueous solution dropwise. Ethyl acetate (10 L) was added and the reaction solution was stirred for 10 min. The reaction solution was filtered, and the filter cake was washed with ethyl acetate (12.5 L). The aqueous phase was extracted with ethyl acetate (10 L×3), and the combined organic phase was concentrated under reduced pressure at 45° C. N-heptane (10 L) was added to the concentration residue for pulping, followed by suction filtration to obtain a brown-red solid. The solid was dried in a vacuum drying oven (40° C.) to obtain compound 1-4c.

MS-ESI $(M+H)^+$: calculated 222, 224, and measured 222, 224.

Step 3:

A solvent N, N-dimethylacetamide (10 L) was added to a reactor (50 L) and compound 1-4c (1003.65 g) was added under stirring. The internal temperature was controlled to bellow 55° C., at which sodium thiomethoxide (1276.97 g) was slowly added to the reactor (50 L) in batches; and the reaction mixture was stirred at 50° C. for 30 min. The reactor temperature was raised to 120° C., at which time the internal temperature was 109° C., and the reactor was stirred for 12 h under this condition. The reactor temperature was adjusted to 50° C., so that the reaction solution temperature was dropped to 40 to 50° C.; the reaction solution was filtered with diatomite and washed with ethyl acetate (10 L); and the filtrate was added with water (10 L) and extracted with ethyl acetate (5 L×2) to obtain an aqueous phase. The aqueous phase was adjusted to pH=7 with concentrated hydrochloric acid and extracted with ethyl acetate (5 L×2); and the organic phases were combined, washed with water (10 L×3), and concentrated under reduced pressure until the weight did not change to obtain compound 1-4d.

MS-ESI $(M+H)^+$: calculated 176, and measured 176.

Step 4:

Dichloromethane (8 L) was added to a cleaned 50 L high- and low-temperature reactor and stirred. Compound 1-4d (1474.02 g) was added to the reactor, and the temperature of an oil bath was adjusted such that the temperature in the reactor was controlled at 0 to 10° C. Concentrated hydrochloric acid (4.38 L) was slowly added to the reactor in batches, and the internal temperature was controlled at 5 to 15° C. After the addition of the concentrated hydrochloric acid was completed, the temperature in the reactor was dropped to −5° C. A sodium hypochlorite aqueous solution (21.35 L) was slowly added dropwise to the reactor in batches, and the whole process was controlled at 0 to 10° C. The reaction solution was filtered, and the filter cake was washed with methyl tert-butyl ether (2 L×2) and then collected. The collected filter cake was put into a drying oven and dried to obtain compound 1-4e.

MS-ESI $(M+H)^+$: calculated 242, and measured 242.

Step 5:

Dichloromethane (10 L) was added to a 50 L reactor and stirred; the internal temperature was controlled at 0 to 10° C., and compound 1-4e (1462.35 g) was added into the reactor. The internal temperature was controlled at 0 to 10° C. and N, N-diisopropylethylamine (934.63 g) was slowly added dropwise into the reaction solution; and the internal temperature was controlled at 0 to 10° C., and compound 1-4f (1230.24 g) was slowly added to the reaction solution in batches. Upon the completion of addition, the temperature was raised to 10 to 20° C. and the mixture was further stirred for 0.5 h. The organic phase was washed with a saturated ammonium chloride aqueous solution (3 L×3), and the combined saturated ammonium chloride aqueous solution was extracted with dichloromethane (3 L). The organic phases were separately concentrated under reduced pressure until the weight did not change, and then dried with a vacuum drying oven to obtain compound 1-4g.

MS-ESI $(M+H)^+$: calculated 392, and measured 392.

Step 6:

3.1 L of anhydrous dichloromethane was added to a cleaned 5 L three-necked flask and stirred. The weighed compound 1-4g (451.34 g) was added to the reaction flask; and after the solid was dissolved, put the reaction flask into an ice water bath such that the internal temperature of the reaction system was reduced to 0° C. The weighed m-chloroperoxybenzoic acid (429.81 g) was slowly added to the 5 L reaction flask in batches, and the temperature was kept at 0 to 10° C. throughout the process. After the addition of the m-chloroperoxybenzoic acid was completed, the ice water bath of the reaction flask was removed and replaced with an oil bath, and the internal temperature of the reaction flask was stabilized at 20 to 25° C. and stirred for 12 h. The reaction flask was put in an ice water bath and stirred for 1 h, and filtered; the filter cake was rinsed with dichloromethane (400 mL×2); a 10% sodium thiosulfate aqueous solution was added dropwise to the filtrate at 25 to 30° C. until the starch potassium iodide test strip did not change blue; and a saturated sodium bicarbonate aqueous solution was added dropwise to the system till pH=7. The mixture was allowed to stand for stratification, the organic phase was reserved, and the aqueous phase was extracted once with 3 L of dichloromethane. The organic phases were combined, washed with a 1% sodium bicarbonate aqueous solution (4 L×10), dried with anhydrous sodium sulfate, and filtered; and the filtrate was concentrated under reduced pressure. The solid obtained by the concentration was dried in the drying oven to obtain compound 1-4h.

MS-ESI $(M+H)^+$: calculated 408, and measured 408.

Step 7:

Compound 1-4h (301.42 g) and tetrahydrofuran (1.5 L) were added to a 5 L three-necked flask and stirred well, and triethylamine (206 mL) was added dropwise at an internal temperature of 10 to 20° C. and stirred well. Trifluoroacetic anhydride (206 mL) was added dropwise at an internal temperature of 20 to 30° C. and reacted for 0.5 h at 20 to 30° C. The reaction solution was added with water (1.5 L) and stirred well, and the reaction solution became turbid. Solid sodium hydroxide (600 g) was added at an internal temperature of 40 to 50° C. and stirred for 0.5 h, and a large amount of solid was precipitated; and 1.5 L of methyl tert-butyl ether was added and stirred for 0.5 h. The reaction solution was separated, and the upper organic phase was filtered to obtain a solid. The solid was pulped with methyl tert-butyl ether/ethyl acetate (4.4 L, 10:1) to obtain a slurry which was then filtered to obtain a white solid. The white solid was dried in the drying oven to obtain a crude product of compound 1-4 (371.52 g). Tetrahydrofuran (7 L) was added to a 50 L reactor, the internal temperature was controlled at 20 to 25° C., and the crude product of compound 1-4 (1713.19 g, combined with other batches) was added and stirred at the internal temperature of 20 to 25° C. for 0.5 h, followed by addition of 8.6 L of water, stirring at 20 to 25° C. for 0.5 h, addition of solid sodium hydroxide (800 g), and stirring at the internal temperature of 20 to 25° C. for 0.5 h. Methyl tert-butyl ether (8.6 L) was added and stirred at the internal temperature of 20 to 25° C. for 0.5 h. The solution was separated, the upper organic phase was filtered, the solid obtained in the filtration was reserved, and the solid was dried in the drying oven to a constant weight to obtain compound 1-4.

MS-ESI $(M+4H)^+$: calculated 408, and measured 408.

Example 1: Preparation of Crystal Form A of Compound of Formula (II)

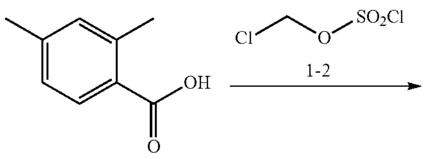

1-1

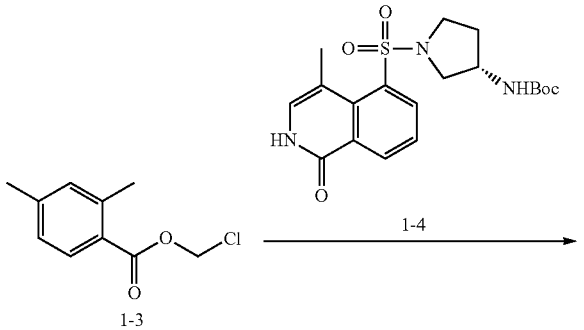

1-3

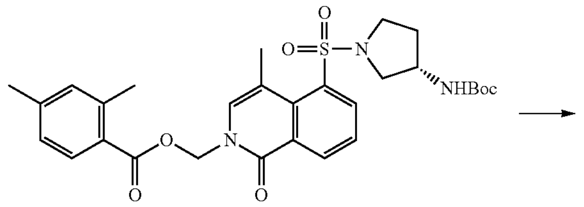

1-5

-continued

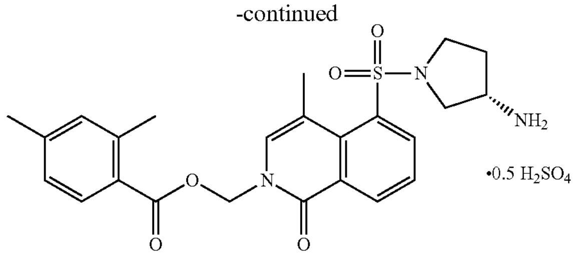

(II)

Step 1:

Under stirring and nitrogen protection, dichloromethane (8.6 L), water (8.6 L), and a starting material 1-1 (575.34 g) were added to a reactor sequentially. The temperature in the reactor was controlled at 10 to 15° C., and sodium bicarbonate (1289.36 g), tetrabutylammonium hydrogen sulfate (133.87 g) and a starting material 1-2 (760.25 g) were added to the reactor sequentially, and stirred for 2 hours at the internal temperature of 10 to 15° C. The reaction solution was allowed to stand for stratification, and the organic phase was concentrated under reduced pressure until no fractions flowed out. The concentrated solution was transferred to a three-necked flask and stirred at an internal temperature of 60 to 70° C. for 12 h, and then naturally cooled to room temperature to obtain a crude product. The crude product was quickly filtered with silica gel and rinsed with dichloromethane until there was no product residue. The eluate was concentrated to about 1.2 L under reduced pressure, and then washed with a 1% sodium bicarbonate aqueous solution (3 L); the organic phase was dried with anhydrous sodium sulfate (500 g), filtered, and then concentrated under reduced pressure until no fractions flowed out, to obtain an intermediate 1-3 which was directly used in the next step without purification.

MS-ESI $(M+H)^+$: calculated 199, and measured 199.

$^1$H NMR (400 MHz, $CD_3Cl$) δ 7.81-7.79 (d, J=8 Hz, 1H), 7.01-6.95 (m, 2H), 5.84 (s, 2H), 2.52 (s, 3H), 2.27 (s, 3H).

Step 2:

2-methyltetrahydrofuran (9702 mL) was added to a reactor and stirred, and the internal temperature was controlled at 10 to 20° C.; and then compound 1-4 (1078.26 g), cesium carbonate (1017.63 g) and the intermediate 1-3 (631.71 g) were added sequentially. The temperature in the reactor was raised to 57 to 63° C., and the mixture was stirred for 2 h and 40 min before the reaction was stopped. The temperature in the reactor was reduced to 15 to 25° C., and then the reaction solution was added with water (10.78 L), stirred and allowed to stand for stratification; the resulting aqueous phase was extracted twice with 2-methyltetrahydrofuran (5390 mL×2); and the combined organic phase was concentrated under reduced pressure to approximately 2.2 L. The concentrated solution was added with acetone (1078 mL) and n-heptane (2156 mL) and further concentrated until no fractions flowed out, to obtain a loose solid. The internal temperature was controlled at 10 to 30° C., and the solid was pulped and stirred for three times with a mixed solvent (11.0495 L, acetone: n-heptane=1:40), filtered, and rinsed with n-heptane (1078 mL). The filter cake was dried under vacuum to constant weight to obtain an intermediate 1-5.

MS-ESI $(M+H)^+$: calculated 570, and measured 570.

$^1$H NMR (400 MHz, $CD_3Cl$) δ 8.86-8.78 (m, 1H), 8.13-8.04 (m, 1H), 7.93-7.86 (m, 1H), 7.58-7.49 (m, 1H), 7.39-7.32 (m, 1H), 7.09-6.99 (m, 2H), 6.14 (s, 2H), 4.86-4.76 (m, 1H), 4.42-4.30 (m, 1H), 3.73-3.61 (m, 2H), 3.57-3.47 (m,

1H), 3.46-3.37 (m, 1H), 2.76-2.67 (m, 3H), 2.59 (s, 3H), 2.39-2.29 (m, 4H), 2.09-1.97 (m, 1H), 1.46 (s, 9H).

Step 3:

Anhydrous tetrahydrofuran (4.24 L) and concentrated sulfuric acid (712.43 g) were added sequentially to a 5 L three-necked flask with an internal temperature controlled at 20 to 30° C., and stirred well for later use. The intermediate 1-5 (1062.15 g) and tetrahydrofuran (4.24 L) were sequentially added to the reactor with the internal temperature controlled at 20 to 30° C., and stirred well. Then, a pre-prepared sulfuric acid in tetrahydrofuran solution was added dropwise to the system, then the reaction was stirred for 4 h with the internal temperature controlled at 35 to 45° C., and a large amount of white precipitate was gradually precipitated in the system. Methyl tert-butyl ether (8.48 L) was slowly added to the reactor and stirred for 0.5 h with the internal temperature controlled at 20 to 30° C.; the reaction solution was filtered, and the filtered solid was pulped sequentially with a mixed solvent (methyl tert-butyl ether/tetrahydrofuran=10.6 L/10.6 L) and methyl tert-butyl ether (21.2 L) at 20 to 30° C. for 0.5 h, and then pulped with water for five times (21.2 L×5) sequentially till the pH of the filtrate was about 7. The internal temperature was controlled at 20 to 30° C., and the solid was pulped sequentially in methyl tert-butyl ether (15.9 L) and a mixed solvent (methyl tert-butyl ether/tetrahydrofuran=10.6 L/5.3 L), and then filtered, rinsed and dried in vacuum at 45° C. or lower to obtain the crystal form A of the compound of formula (II). The sulfate radical content was 9.17% detected by ion chromatography. Therefore, it was inferred that there was also 0.5 sulfate salt in the compound of formula (II).

MS-ESI $(M+H)^+$: calculated 470, and measured 470. $^1H$ NMR (400 MHz, DMSO-d&) S 8.64-8.58 (m, 1H), 8.26 (d, J=8 Hz, 1H), 7.74-7.62 (m, 3H), 7.16-7.11 (m, 1H), 7.11-7.05 (m, 1H), 6.08 (s, 2H), 3.94-3.89 (m, 1H), 3.70-3.55 (m, 2H), 3.55-3.44 (m, 1H), 3.43-3.27 (m, 1H), 2.59 (s, 3H), 2.48-2.45 (m, 3H), 2.35-2.29 (m, 1H), 2.29-2.24 (m, 3H), 2.16-1.90 (m, 1H).

Figure 2:
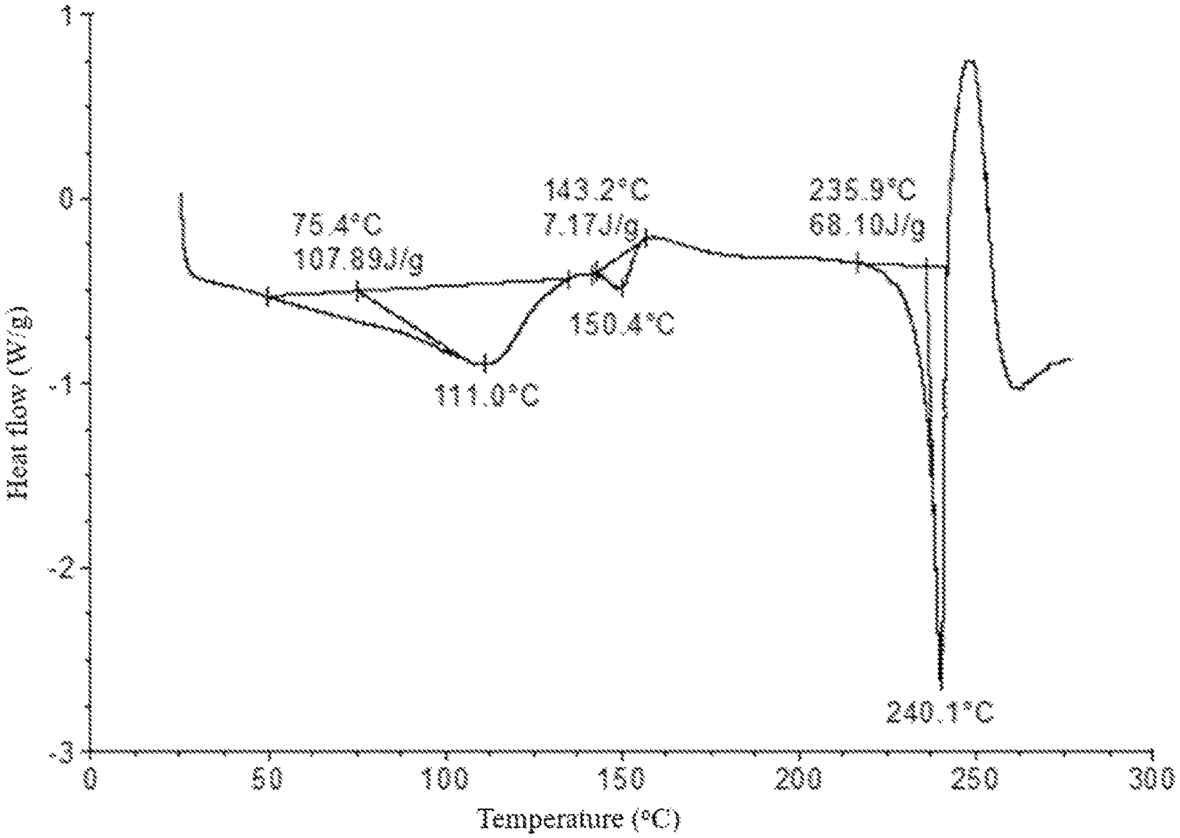
FIG. 2 is a DSC pattern of the crystal form A of the compound of formula (II)
Figure 3:
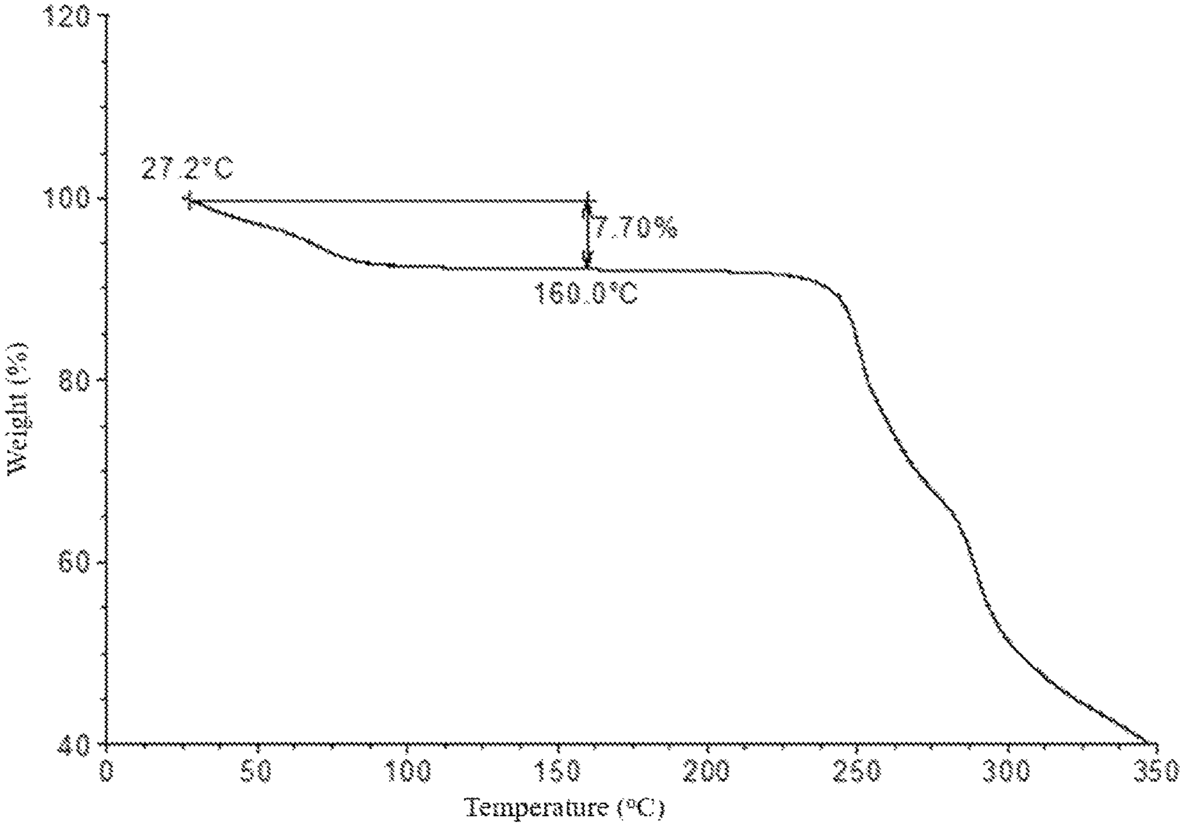
FIG. 3 is a TGA pattern of the crystal form A of the compound of formula (II)

Characterization of crystal form A of compound of formula (II):

(1) X-ray powder diffraction assay: the test results are shown in FIG. 1 and Table 1;

(2) differential scanning calorimetry assay: the test results are shown in FIG. 2; and (3) thermal gravimetric analysis assay: the test results are shown in FIG. 3.

Example 2: Preparation of Compound of Formula (I)

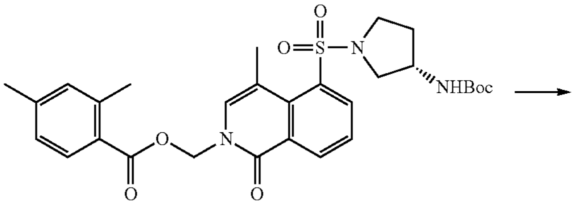

1-5

-continued

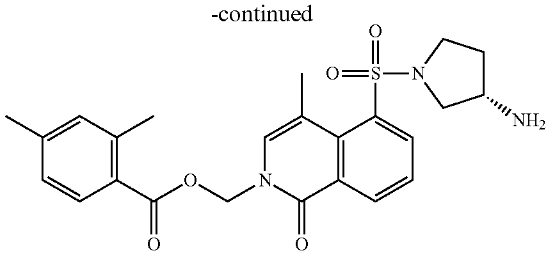

Compound of formula (I)

Compound 1-5 (2.2 g, 3.84 mmol) was dissolved in ethyl acetate (35 mL), and a hydrogen ethyl acetate solution (4 M, 20 mL) was added to the reaction solution and stirred at 15° C. for 12 h. The reaction solution was added with a saturated sodium bicarbonate aqueous solution to adjust pH to 8, and extracted with ethyl acetate (60 mL×2); the organic phase was dried with anhydrous sodium sulfate (5 g), filtered, and concentrated under reduced pressure to obtain a crude product; and the crude product was purified by high performance liquid chromatography (neutral system) to obtain the compound of formula (I). MS-ESI $[M+H]^+$: calculated 470, and measured 470. $^1H$ NMR (400 MHz, $CD_3OD$) δ=8.71 (dd, J=1.4, 8.0 Hz, 1H), 8.24 (dd, J=1.5, 7.8 Hz, 1H), 7.81 (d, J=7.9 Hz, 1H), 7.64 (t, J=7.9 Hz, 1H), 7.54 (d, J=0.9 Hz, 1H), 7.09 (s, 1H), 7.05 (d, J=7.9 Hz, 1H), 6.14 (s, 2H), 3.77-3.62 (m, 3H), 3.59-3.50 (m, 1H), 3.20 (dd, J=4.9, 9.5 Hz, 1H), 2.70 (d, J=0.9 Hz, 3H), 2.53 (s, 3H), 2.32 (s, 3H), 2.30-2.23 (m, 11H), 1.96-1.86 (m, 1H).

Example 3: Preparation of Crystal Form B of Compound of Formula (II)

An appropriate amount of the crystal form A of the compound of formula (II) was weighed and put in a sample bottle, and a certain volume of solvent in Table 3 was added to prepare suspensions or solutions of different single solvents. After the suspension was stirred continuously at 50° C. for 3 h, the sample was filtered and the filtered solid was dried in vacuum in a vacuum drying oven at 45° C. to remove the residual solvent.

TABLE 3

Preparation of crystal form B of compound of formula (II)

| No. | Solvent | Sample amount | Solvent volume | State | Crystal form |
|---|---|---|---|---|---|
| 1 | Isopropanol | 100 | 2.0 | Suspension | Crystal form B |
| 2 | Tetrahydrofuran | 100 | 2.0 | Suspension | Crystal form B |
| 3 | Acetonitrile | 101 | 2.0 | Suspension | Crystal form B |
| 4 | 2-butanone | 100 | 2.0 | Suspension | Crystal form B |
| 5 | Ethyl acetate | 101 | 2.0 | Suspension | Crystal form B |

Figure 4:
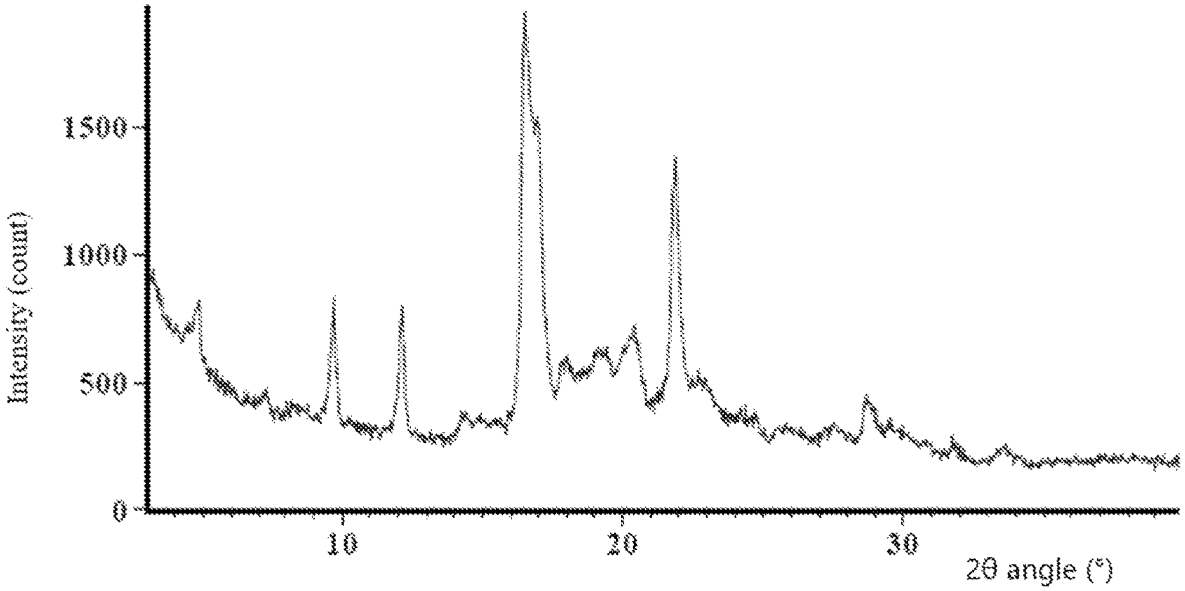
FIG. 4 is an XRPD pattern of a crystal form B of the compound of formula (II) under Cu-Kα radiation.
Figure 5:
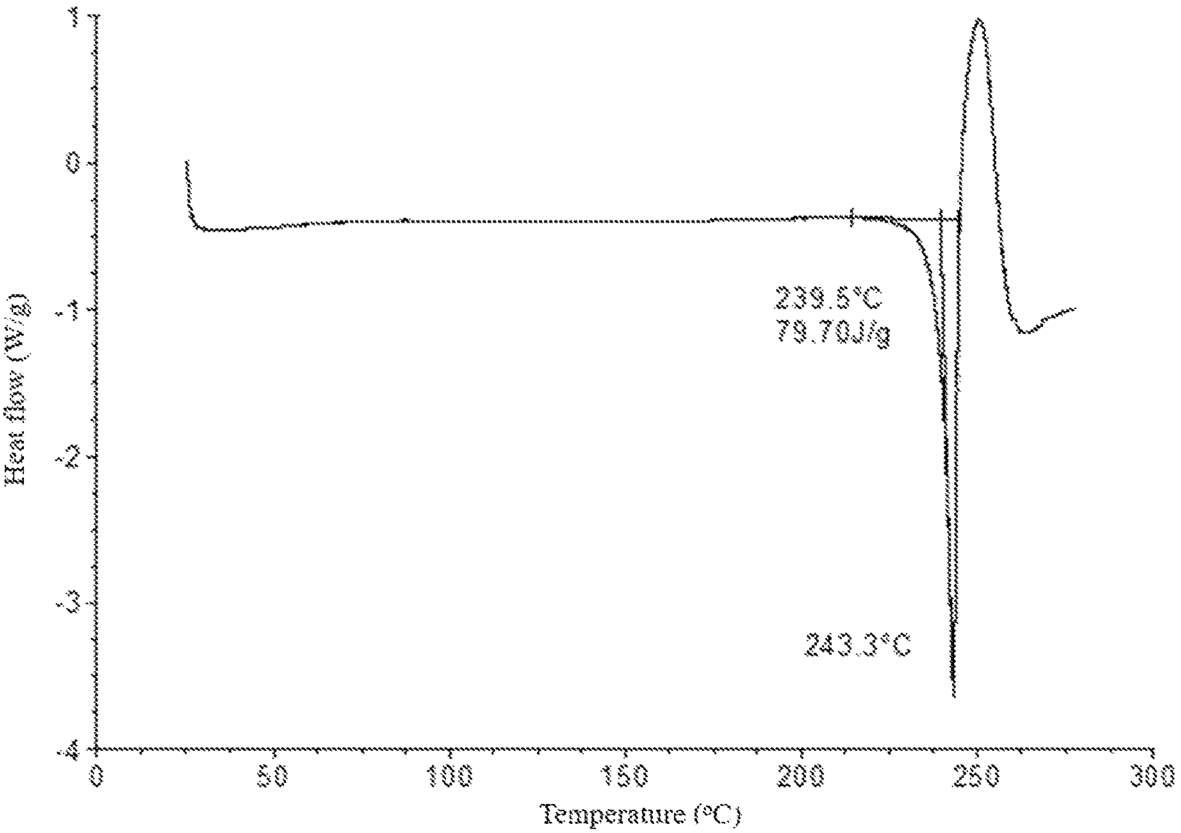
FIG. 5 is a DSC pattern of the crystal form B of the compound of formula (II)
Figure 6:
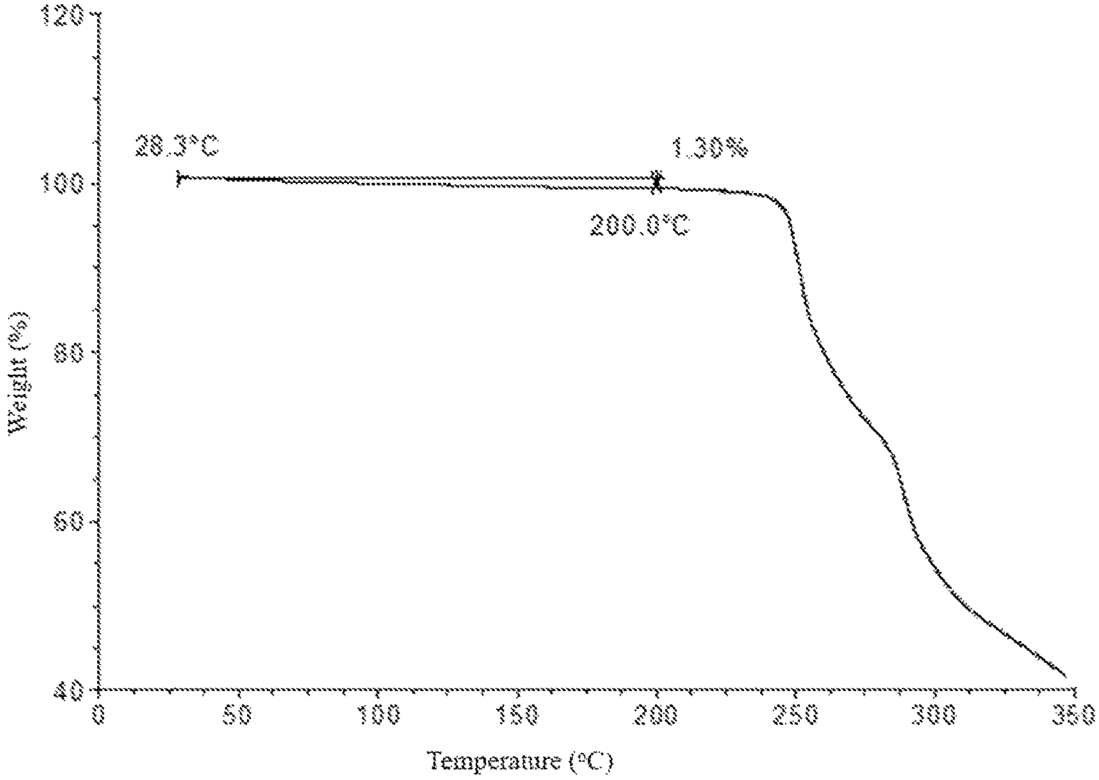
FIG. 6 is a TGA pattern of the crystal form B of the compound of formula (II)

Characterization of crystal form B of compound of formula (II):

(1) X-ray powder diffraction assay: the test results are shown in FIG. 4 and Table (2) differential scanning calorimetry assay: the test results are shown in FIG. 5; and (3) thermal gravimetric analysis assay: the test results are shown in FIG. 6.

Example 4: Hygroscopicity Research on Crystal Form B of Compound of Formula (II)

Experimental Materials:

SMS DVS intrinsic dynamic vapor sorption instrument

Experimental Method:

10 to 15 mg of the crystal form B of the compound of formula (II) was put in a DVS sample tray for testing.

Figure 7:
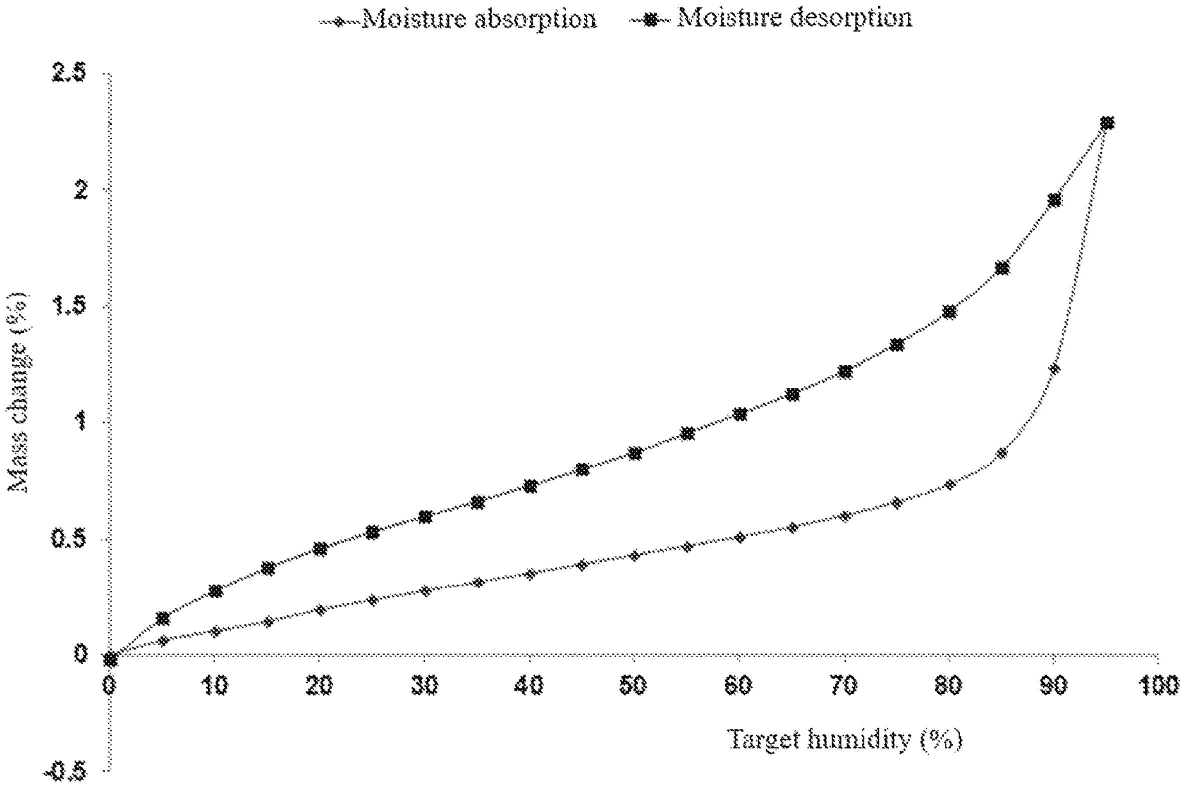
FIG. 7 is a DVS pattern of the crystal form B of the compound of formula (II).

Experimental Results:

A DVS pattern of the crystal form B of the compound of formula (II) is shown in FIG. 7, where $\Delta W=0.736\%$.

Experimental Conclusion:

The crystal form B of the compound of formula (II) had a hygroscopic weight gain of 0.736% at 25° C. and 80% RH, demonstrating slightly hygroscopic.

Example 5: Solid Stability Research on Crystal Form B of Compound of Formula (II)

The crystal form B of the compound of formula (II) was placed at 40° C./75% RH (sealed with a double-layer LDPE bag and further heat-sealed with an aluminum foil bag) for 6 months, and placed at 25° C./60% RH (sealed with a double-layer LDPE bag and further heat-sealed with an aluminum foil bag) for 12 months, respectively. The crystal form was tested individually at each sampling point to determine the crystal form stability of the sample.

TABLE 4

Experimental results of solid stability research on crystal form B of compound of formula (II)

| Experimental conditions | Inspection time | Crystal form |
|---|---|---|
| 40° C. ± 2° C./ 75% RH ± 5% RH | 3 months | Crystal form B |
| | 6 months | Crystal form B |
| 25° C. ± 2° C./ 60% RH ± 5% RH | 3 months | Crystal form B |
| | 6 months | Crystal form B |
| | 12 months | Crystal form B |

Conclusion: the crystal form B of the compound of formula (II) had good stability in accelerated and long-term tests.

Biological Testing Experiments

Experimental Example 1: Pharmacokinetic Test in Aqueous Humor

Experimental Objective:

The compound was a prodrug molecule containing an ester functional group, which can be hydrolyzed into an active drug molecule (parent drug) under the action of abundant ester hydrolase in the eye tissue when administered with eye drops. In this experiment, the production rate of the active pharmaceutical ingredients in vivo and the exposure amount of the active pharmaceutical ingredients were detected.

Experimental Materials:

Male New Zealand white rabbits, aged 3 to 6 months, weighted 2.0 to 5.0 kg, purchased from Pizhou Oriental Breeding Co., Ltd.

Preparation of Eye Drop Sample:

The used solvent was 1.2% hydroxypropyl methylcellulose E5/20.5% poloxamer P407/1.6% poloxamer P188.

Experimental Operation:

The dosage of eye drops was 0.5 mg/eye, administrated in both eyes. Aqueous humor samples were collected at 0.25 h, 0.5 h, 2 h, 4 h, 8 h, and 24 h after administration. All samples were quantitatively detected by liquid chromatography coupled with mass spectrometry-mass spectrometry in the aqueous humor of the experimental animals. The measured concentration values were calculated by WinNonlin non-compartment model according to the concentration-time data of aqueous humor, such as half-life, peak concentration, peak time, unit exposure amount of aqueous humor, etc.

TABLE 5

Pharmacokinetic test results in aqueous humor of New Zealand rabbits

| Test article | Peak concentration of drug in aqueous humor (nM) | Half-life (h) | Peak time of drug in aqueous humor (h) | Unit exposure amount (nM · h) |
|---|---|---|---|---|
| Compound of formula (I) | 7470 | 2.72 | 2.0 | 36581 |
| Control compound 2 | 868 | — | 2.0 | 3555 |

"—": Not detected.

Conclusion: the results showed that the active metabolites after hydrolysis of esters were mainly detected in aqueous humor instead of the tested compounds (prodrug molecules); the compound of formula (I) significantly increased the exposure amount of the active drug, and the peak concentration and action time of drugs in blood were significantly prolonged.

Experimental Example 2: Intraocular Pressure Reduction Test for New Zealand Rabbits Suffered with Acute Intraocular Hypertension Experimental Objective:

Acute intraocular hypertension was induced for rabbits by injection of a viscoelastic agent into the anterior chamber, and the effects of ocular pressure reduction of the compound of formula (I) were inspected by administration of eye drops at different concentrations.

Experimental Materials:

Male New Zealand white rabbits, aged 97 to 127 days, weighted 2.5 to 3.4 kg, purchased from Pizhou Oriental Breeding Co., Ltd.

Experimental Operation:

50 male New Zealand white rabbits were randomly divided into 5 groups according to body weight, 10 rabbits/group. The anterior chambers of the right eyes of animals in Groups 1 to 5 were injected with medical sodium hyaluronate gel in a single dose, 100 μL/eye, to induce ocular hypertension in the animals. In 5 to 15 min after molding, the right eye was administrated dropwise with the solvent, K-115, and the test article (compounds of formula (I) of different concentrations), and the left eye was administrated dropwise with the solvent, 50 μL/eye; and the intraocular pressures of the animals in both eyes were measured before administration, as well as at 2, 4, 6, 8, and 10 h after administration, respectively. The experimental results are shown in Table 6.

TABLE 6

Change results of intraocular pressure (Mean ± SEM) in both eyes before and after modeling and administration of animals in the groups

| Measured intraocular pressure | | Before administration | 2 h after administration | 4 h after administration | 6 h after administration | 8 h after administration | 10 h after administration |
|---|---|---|---|---|---|---|---|
| Negative control | Intraocular pressure in left eye (mmHg) | 9.93 | 6.40 | 6.97 | 9.83 | 12.03 | 13.63 |
| | Intraocular pressure in right eye (mmHg) | 10.57 | 8.57 | 14.00 | 17.67 | 16.30 | 15.87 |
| K-115 4 mg/mL | Intraocular pressure in left eye (mmHg) | 11.80 | 6.50 | 8.54 | 11.40 | 13.20 | 13.37 |
| | Intraocular pressure in right eye (mmHg) | 11.77 | 8.20 | 11.27 | 15.07 | 15.57 | 16.47 |
| Compound of formula (I) 0.25 mg/mL | Intraocular pressure in left eye (mmHg) | 10.53 | 6.07 | 6.60 | 9.10 | 11.50 | 12.43 |
| | Intraocular pressure in right eye (mmHg) | 11.43 | 8.47 | 8.60 | 11.20 | 13.37 | 13.10 |
| Compound of formula (I) 2.0 mg/mL | Intraocular pressure in left eye (mmHg) | 11.27 | 6.60 | 7.04 | 11.23 | 12.84 | 13.10 |
| | Intraocular pressure in right eye (mmHg) | 11.23 | 8.52 | 11.56 | 13.81 | 12.96 | 11.96 |
| Compound of formula (I) 8.0 mg/mL | Intraocular pressure in left eye (mmHg) | 11.20 | 5.93 | 6.43 | 10.10 | 11.87 | 13.19 |
| | Intraocular pressure in right eye (mmHg) | 11.53 | 7.40 | 7.97 | 8.84 | 8.60 | 8.78 |

Conclusion: in the acute intraocular hypertension model, the compound of formula (I) demonstrated good intraocular pressure reduction effects at different test doses, and had a certain dose correlation at the same time, and the intraocular pressure reduction amplitude and the sustained effect were both better than those of K-115.

Experimental Example 3: Intraocular Pressure Reduction and Ocular Toxicity Test with New Zealand Rabbits with Normal Intraocular Pressure by Repeated Administration of Eye Drops for 14 Days Experimental Objective:

An intraocular pressure reduction effect and potential ocular toxicity of the compound of formula (I) were inspected with rabbits with normal intraocular pressure by repeated administration of eye drops for 14 days.

Experimental Materials:

Male New Zealand white rabbits, aged 97 to 127 days, weighted 2.6-3.5 kg, purchased from Pizhou Oriental Breeding Co., Ltd.

Experimental Operation I:

The Male New Zealand white rabbits were randomly divided into 7 groups according to body weights, 6 rabbits/group. The animals in Groups 1 to 7 were administrated dropwise with a solvent/control/test article in both eyes in an administration volume of 50 μL/eye, once a day for 14 consecutive days, and the day of first administration was recorded as Day 1. The intraocular pressures of the animals were measured before administration, as well as at 1, 2, 4, 6, 8 and 10 h after administration, respectively. On Days 2 to 14, the intraocular pressures of animals in the K-115 administration group were measured at 1 h after daily administration; and intraocular pressures of the animals in the remaining groups were measured at 4 h after daily administration. The experimental results are shown in Tables 7, 8, and 9:

TABLE 7

Changes of intraocular pressures (Mean ± SEM) of animals in respective groups in both eyes before and after administration on Day 1

| Measured intraocular pressure | | Before administration | 1 h after administration | 2 h after administration | 4 h after administration | 6 h after administration | 8 h after administration | 10 h after administration |
|---|---|---|---|---|---|---|---|---|
| Negative control | Average intraocular pressure in both eyes (mmHg) | 9.89 | 10.31 | 10.97 | 11.31 | 11.94 | 12.97 | 14.42 |
| K-115 4 mg/mL | Average intraocular pressure in both eyes (mmHg) | 10.83 | 7.72 | 9.00 | 9.67 | 10.56 | 10.28 | 12.81 |
| | Change in intraocular pressure (mmHg) | −0.94 | 2.59 | 1.97 | 1.64 | 1.38 | 2.69 | 1.61 |
| Compound of formula (I) 0.5 mg/mL | Average intraocular pressure in both eyes (mmHg) | 10.11 | 8.83 | 7.56 | 7.11 | 9.61 | 9.06 | 9.97 |
| | Change in intraocular pressure (mmHg) | −0.22 | 1.48 | 3.41 | 4.2 | 2.33 | 3.91 | 4.45 |

TABLE 7-continued

Changes of intraocular pressures (Mean ± SEM) of animals in respective groups in both eyes before and after administration on Day 1

| Measured intraocular pressure | | Measurement time point | | | | | | |
|---|---|---|---|---|---|---|---|---|
| | | Before administration | 1 h after administration | 2 h after administration | 4 h after administration | 6 h after administration | 8 h after administration | 10 h after administration |
| Compound of formula (I) 1.0 mg/mL | Average intraocular pressure in both eyes (mmHg) | 9.94 | 7.08 | 6.67 | 6.44 | 8.00 | 9.22 | 10.56 |
| | Change in intraocular pressure (mmHg) | −0.05 | 3.23 | 4.3 | 4.87 | 3.94 | 3.75 | 3.86 |
| Compound of formula (I) 2.0 mg/mL | Average intraocular pressure in both eyes (mmHg) | 9.67 | 8.56 | 7.47 | 7.47 | 7.25 | 8.44 | 9.67 |
| | Change in intraocular pressure (mmHg) | 0.22 | 1.75 | 3.5 | 3.84 | 4.69 | 4.53 | 4.75 |
| Compound of formula (I) 4.0 mg/mL | Average intraocular pressure in both eyes (mmHg) | 9.67 | 10.44 | 7.81 | 6.47 | 6.22 | 7.33 | 8.64 |
| | Change in intraocular pressure (mmHg) | 0.22 | −0.13 | 3.16 | 4.84 | 5.72 | 5.64 | 5.78 |
| Compound of formula (I) 8.0 mg/mL | Average intraocular pressure in both eyes (mmHg) | 10.17 | 7.69 | 6.39 | 7.06 | 7.11 | 7.22 | 7.97 |
| | Change in intraocular pressure (mmHg) | −0.28 | 2.62 | 4.58 | 4.25 | 4.83 | 5.75 | 6.45 |

TABLE 8

Changes of intraocular pressures (Mean ± SEM) of animals in respective groups in both eyes before and after repeated administration from Day 2 to Day 7

| Measured intraocular pressure | | Measurement time point | | | | | |
|---|---|---|---|---|---|---|---|
| | | Day 2 | Day 3 | Day 4 | Day 5 | Day 6 | Day 7 |
| Negative control | Average intraocular pressure in both eyes (mmHg) | 11.08 | 10.39 | 10.61 | 10.97 | 9.31 | 10.06 |
| K-115 4 mg/mL | Average intraocular pressure in both eyes (mmHg) | 6.83 | 6.81 | 6.92 | 6.67 | 6.75 | 7.39 |
| | Change in intraocular pressure (mmHg) | 4.25 | 3.58 | 3.69 | 4.3 | 2.56 | 2.67 |
| Compound of formula (I) 0.5 mg/mL | Average intraocular pressure in both eyes (mmHg) | 7.94 | 7.31 | 7.78 | 7.19 | 6.61 | 6.00 |
| | Change in intraocular pressure (mmHg) | 3.14 | 3.08 | 2.83 | 3.78 | 2.7 | 4.06 |
| Compound of formula (I) 1.0 mg/mL | Average intraocular pressure in both eyes (mmHg) | 7.64 | 7.50 | 7.33 | 7.44 | 6.92 | 7.00 |
| | Change in intraocular pressure (mmHg) | 3.44 | 2.89 | 3.28 | 3.53 | 2.39 | 3.06 |
| Compound of formula (I) 2.0 mg/mL | Average intraocular pressure in both eyes (mmHg) | 7.03 | 7.25 | 6.86 | 6.47 | 5.92 | 5.78 |
| | Change in intraocular pressure (mmHg) | 4.05 | 3.14 | 3.75 | 4.5 | 3.39 | 4.28 |
| Compound of formula (I) 4.0 mg/mL | Average intraocular pressure in both eyes (mmHg) | 6.53 | 5.58 | 5.53 | 6.61 | 5.47 | 5.56 |
| | Change in intraocular pressure (mmHg) | 4.55 | 4.81 | 5.08 | 4.36 | 3.84 | 4.5 |
| Compound of formula (I) 8.0 mg/mL | Average intraocular pressure in both eyes (mmHg) | 6.33 | 5.78 | 5.97 | 6.42 | 5.56 | 5.28 |
| | Change in intraocular pressure (mmHg) | 4.75 | 4.61 | 4.64 | 4.55 | 3.75 | 4.78 |

TABLE 9

Changes of intraocular pressures (Mean ± SEM) of animals in respective groups in both eyes before and after repeated administration from Day 8 to Day 14

| Measured intraocular pressure | | Measurement time point | | | | | | |
|---|---|---|---|---|---|---|---|---|
| | | Day 8 | Day 9 | Day 10 | Day 11 | Day 12 | Day 13 | Day 14 |
| Negative control | Average intraocular pressure in both eyes (mmHg) | 11.31 | 9.44 | 9.75 | 9.69 | 9.53 | 11.39 | 10.97 |
| K-115 4 mg/mL | Average intraocular pressure in both eyes (mmHg) | 7.53 | 7.78 | 7.94 | 7.94 | 7.89 | 8.25 | 8.50 |

TABLE 9-continued

Changes of intraocular pressures (Mean ± SEM) of animals in respective groups in both eyes before and after repeated administration from Day 8 to Day 14

| Measured intraocular pressure | | Measurement time point | | | | | | |
|---|---|---|---|---|---|---|---|---|
| | | Day 8 | Day 9 | Day 10 | Day 11 | Day 12 | Day 13 | Day 14 |
| | Change in intraocular pressure (mmHg) | 3.78 | 1.66 | 1.81 | 1.75 | 1.64 | 3.14 | 2.47 |
| Compound of formula (I) 0.5 mg/mL | Average intraocular pressure in both eyes (mmHg) | 7.11 | 6.19 | 6.75 | 6.44 | 6.25 | 8.08 | 7.25 |
| | Change in intraocular pressure (mmHg) | 4.2 | 3.25 | 3 | 3.25 | 3.28 | 3.31 | 3.72 |
| Compound of formula (I) 1.0 mg/mL | Average intraocular pressure in both eyes (mmHg) | 7.28 | 6.94 | 7.31 | 7.50 | 6.89 | 8.06 | 7.44 |
| | Change in intraocular pressure (mmHg) | 4.03 | 2.5 | 2.44 | 2.19 | 2.64 | 3.33 | 3.53 |
| Compound of formula (I) 2.0 mg/mL | Average intraocular pressure in both eyes (mmHg) | 6.78 | 5.72 | 5.94 | 6.03 | 6.03 | 7.11 | 7.06 |
| | Change in intraocular pressure (mmHg) | 4.53 | 3.72 | 3.81 | 3.66 | 3.5 | 4.28 | 3.91 |
| Compound of formula (I) 4.0 mg/mL | Average intraocular pressure in both eyes (mmHg) | 6.78 | 5.47 | 5.08 | 5.83 | 5.89 | 7.03 | 6.33 |
| | Change in intraocular pressure (mmHg) | 4.53 | 3.97 | 4.67 | 3.86 | 3.64 | 4.36 | 4.64 |
| Compound of formula (I) 8.0 mg/mL | Average intraocular pressure in both eyes (mmHg) | 5.72 | 5.19 | 5.56 | 5.53 | 5.56 | 6.67 | 6.94 |
| | Change in intraocular pressure (mmHg) | 5.59 | 4.25 | 4.19 | 4.16 | 3.97 | 4.72 | 4.03 |

Conclusion: single administration of the compound of formula (I) demonstrated better efficacy (highest intraocular pressure reduction effect and longest action time) at all tested doses (0.5 to 8.0 mg/mL), which was significantly better than that of K-115. In the case of 14 days of consecutive administration, the compound of formula (I) could consistently maintain a significant intraocular pressure reduction effect at a dose of 0.5 mg/mL, which was still significantly better than that of K-115 in the evaluation of peak (Cmax) intraocular pressure reduction effect.

Experimental Operation II:

42 male New Zealand white rabbits were randomly grouped into 7 groups according to body weights, 6 rabbits/group. Among the animals in Groups 1-7, the left eye was administrated dropwise with normal saline, and the right eye was administrated dropwise with a solvent/control/test article in an administration volume of 50 μL/eye respectively, once a day for 14 consecutive days, and the day of first administration was recorded as Day 1. The intraocular pressures of the animals were measured before administration on Day 1, as well as at 1 h, 2 h, 4 h, 6 h, 8 h and 10 h after administration on Day 1 (Table 10).

Animals were subjected to eye irritation response detection and fluorescein sodium detection (scored according to scoring criteria) in both eyes with a hand-held slit lamp before the start of test (Day −2/Day −1), before daily administration (Day 1 to Day 14), and at 1 h, 2 h, 4 h, 24 h, 48 h, and 72 h after the last administration (Day 14).

TABLE 10

Changes of intraocular pressures (Mean ± SEM) of animals in respective groups in both eyes before and after administration on Day 1

| Intraocular pressure measurements | | Measurement time point | | | | | | |
|---|---|---|---|---|---|---|---|---|
| | | Before administration | 1 h after administration | 2 h after administration | 4 h after administration | 6 h after administration | 8 h after administration | 10 h after administration |
| Negative controls | Average intraocular pressure in both eyes (mmHg) | 9.33 | 8.89 | 9.56 | 9.89 | 10.78 | 10.39 | 12.17 |
| K-115 4 mg/mL | Average intraocular pressure in both eyes (mmHg) | 10.17 | 5.50 | 7.06 | 9.00 | 9.17 | 10.61 | 12.33 |
| | Change in intraocular pressure (mmHg) | 0.83 | −3.39 | −2.50 | −0.89 | −1.61 | 0.23 | 0.17 |
| Compound of formula (I) 0.25 mg/mL | Average intraocular pressure in both eyes (mmHg) | 9.84 | 6.22 | 6.17 | 6.67 | 8.06 | 9.72 | 10.95 |
| | Change in intraocular pressure (mmHg) | 0.50 | −2.67 | −3.39 | −3.22 | −2.72 | −0.66 | −1.22 |
| Compound of formula (I) 0.5 mg/mL | Average intraocular pressure in both eyes (mmHg) | 9.22 | 5.39 | 5.50 | 6.95 | 8.94 | 9.89 | 11.56 |
| | Change in intraocular pressure (mmHg) | −0.11 | −3.50 | −4.05 | −2.94 | −1.84 | −0.50 | −0.61 |
| Compound of formula (I) 1.0 mg/mL | Average intraocular pressure in both eyes (mmHg) | 9.17 | 5.56 | 5.39 | 6.67 | 7.33 | 10.50 | 10.89 |
| | Change in intraocular pressure (mmHg) | −0.17 | −3.33 | −4.17 | −3.22 | −3.45 | 0.11 | −1.28 |

TABLE 10-continued

Changes of intraocular pressures (Mean ± SEM) of animals in respective groups in both eyes before and after administration on Day 1

| Intraocular pressure measurements | | Measurement time point: Before administration | 1 h after administration | 2 h after administration | 4 h after administration | 6 h after administration | 8 h after administration | 10 h after administration |
|---|---|---|---|---|---|---|---|---|
| Compound of formula (I) 2.0 mg/mL | Average intraocular pressure in both eyes (mmHg) | 9.72 | 8.11 | 5.84 | 6.06 | 7.11 | 9.00 | 10.05 |
| | Change in intraocular pressure (mmHg) | 0.39 | −0.78 | −3.72 | −3.83 | −3.67 | −1.39 | −2.11 |
| Compound of formula (I) 4.0 mg/mL | Average intraocular pressure in both eyes (mmHg) | 10.00 | 6.61 | 5.84 | 5.72 | 6.61 | 8.39 | 10.67 |
| | Change in intraocular pressure (mmHg) | 0.67 | −2.28 | −3.72 | −4.17 | −4.17 | −2.00 | −1.50 |

Conclusion: single administration of the compound of formula (I) demonstrated better efficacy (highest intraocular pressure reduction effect and longest action time) at all tested doses (0.25 to 4.0 mg/mL), which was significantly better than that of K-15.

Animals were subjected to eye irritation response detection in both eyes with a handheld slit lamp on Day −2 to Day −1 before the start of test, before first administration every day (Day 1 to Day 14), and at 1 h, 2 h, 4 h, 24 h, 48 h, and 72 h after the last administration. The scoring criteria were as follows:

| Eye irritation response | Scores |
|---|---|
| Cornea | |
| Non-turbid | 0 |
| Scatteredly or diffusively turbid, with the iris clearly visible | 1 |
| A translucent area was easy to distinguish, while the iris was blurred | 2 |
| A gray-white translucent area appeared, the iris details were not clear, and pupil size was barely visible | 3 |
| The cornea was opaque and the iris was unrecognizable | 4 |
| Iris | |
| Normal | 0 |
| Markedly deepened rugae, congestion, swlling, mildly circumcorneal hyperaemia, and the pupils still had response to light | 1 |
| Bleeding/visible necrosis/no response to light (or one of them) | 2 |
| Conjunctiva | |
| Hyperemia (referring to the palpebral conjunctiva and bulbar conjunctiva) | |
| Blood vessels were normal | 0 |
| Blood vessels were bloodshot and bright red | 1 |
| Blood vessels were bloodshot and dark red, and not easily distinguished | 2 |
| Blood vessels were diffusively bloodshot and purplish-red | 3 |
| Edema | |
| No edema | 0 |
| Mild edema (including eyelids) | 1 |
| Evident edema with partial eyelid ectropion | 2 |
| Edema to nearly half of eyelids closed | 3 |
| Edema to more than half of eyelids closed | 4 |
| Secretion | |
| No secretion | 0 |
| A small amount of secretion | 1 |
| The secretion made the eyelids and eyelashes moist or sticky | 2 |
| The secretion made the entire eye area moist or sticky | 3 |
| Total maximum score | 16 |

Evaluation of eye irritation response: the maximum scores of cornea, iris, conjunctiva, edema, and secretion were added together to obtain the total score of eye irritation symptoms at each time point for each animal eye. Based on the score of eye irritation symptoms, the average score of each group of animals at each observation time point were calculated, and the degree of eye irritation of each group of animals at each time point was determined according to the following table.

Eye Irritation Evaluation Criteria:

| Scores | Evaluations |
|---|---|
| 0 to 3 | Non-irritating |
| 4 to 8 | Mildly irritating |
| 9 to 12 | Moderately irritating |
| 13 to 16 | Severely irritating |

Fluorescein sodium detection: after irritation response detection for each eye, the fluorescein sodium detection was performed with a handheld slit lamp, and the scoring criteria were as follows:

| Fluorescent staining<br>Fluorescein was used to help diagnose the corneal epithelial injury. A fluorescent stained area may be classified into grades 0 to 4 according to the degree of corneal opacity: | |
|---|---|
| No fluorescent staining. | 0 |
| Local small area of mild fluorescent staining. When viewed with diffused light, the underlying structures of cornea are clearly visible (the pupil margin was clear, and the observation was not affected by fluorescent staining). | 1 |
| Local small area of moderate fluorescent staining. When viewed with diffused light, the structure was clearly visible although some eye details under the cornea were missing. | 2 |
| Obvious fluorescent staining with a relatively large staining area. When viewed with diffused light, the eye structure under the cornea was just identifiable. | 3 |
| Severe fluorescent staining. When viewed with diffused light, the eye structure under the cornea was unrecognizable. | 4 |

Experimental results were as follows:

According to the evaluation criteria of eye irritation, the total score of eye irritation response at each time point in each group was less than 3, and all were classified to be non-irritating according to the criteria.

During the test, the fluorescein sodium test scores of eyes of animals in each group treated with normal saline, a solvent, K-115, and the compound of formula (I) were all less than 1. Animals in each group had staining with a corneal fluorescent staining score of 1 at each treatment and individual time point, which was considered physiological staining. There was no corneal epithelial injury at any time point in all groups.

Conclusion: under the conditions of this test, K-115 was added dropwise to the eyes at a concentration of 4 mg/mL for 14 consecutive days with 50 μl/eye/day, showing no irritation. The compound of formula (I) was added dropwise to the eyes at a concentration of 0.25 to 4 mg/mL for 14 consecutive days with 50 μl/eye/day, showing no irritation.

Experimental Example 4: Toxicokinetic Test

Experimental Objective:

The rate of production of active pharmaceutical ingredients in plasma and exposure amount of the active pharmaceutical ingredients were detected after 14 days.

Experimental Materials:

Male New Zealand white rabbits, aged 3 to 6 months, weighted 2.0 to 5.0 kg, purchased from Pizhou Oriental Breeding Co., Ltd.

Experimental Operation:

After 14 days of consecutive administration, blood samples were collected at 0 hours (before administration) and at 0.5, 1, 2, 4, 8 and 24 hours after administration in the group of compound of formula (I) (8.0 mg/ml) at 14-15 days. Approximately 0.8 mL of whole blood was collected from the ear artery or the hindlimb saphenous vein (or other suitable site) of animal subjected to the toxicokinetic test and placed in a labeled blood collection tube with dipotassium EDTA ($K_2EDTA$) as an anticoagulant. Plasma was obtained by centrifugation at 3000 rpm and 2° C. to 8° C. for 10 min within 60 minutes after blood collection. All samples were quantitatively detected for the content of the administrated compound in the plasma of the experimental animal by a liquid chromatography-mass spectrometry coupling technology.

TABLE 11

Test results of active compounds in plasma of New Zealand rabbits after 14 days of consecutive administration

| Compound No. | Time (h) | Concentration. (ng/ml) Group 1 | Group 2 |
|---|---|---|---|
| Compound of formula (I) | 0.00 | BQL | BQL |
| | 0.50 | 3.63 | 3.44 |
| | 1.00 | 2.87 | 2.20 |
| | 2.00 | 1.80 | 1.66 |
| | 4.00 | 0.934 | 0.818 |
| | 8.00 | BQL | BQL |
| | 24.0 | BQL | BQL |

Note:
BQL indicated being below a detection limit.

Conclusion: at a high dose of 8 mg/mL, the metabolite concentration of the compound of formula (I) was 0.934 ng/mL at 4 h after administration, and was below the detection limit at 8 h after administration, showing high system safety.

What is claimed is:

1. A crystal form of a compound of formula (II), (II)

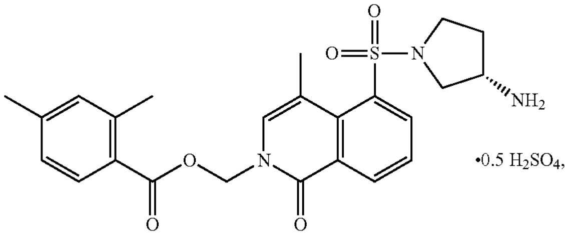

•0.5 $H_2SO_4$, wherein an X-ray powder diffraction pattern of the crystal form has characteristic diffraction peaks at the following angles of 2θ:3.30±0.20°, 6.33±0.20°, 6.55±0.20°, 10.62±0.20°, 12.57±0.20°, and 13.11±0.20°.

2. The crystal form according to claim 1, wherein the X-ray powder diffraction pattern has characteristic diffraction peaks at the following angles of 2θ:3.30±0.20°, 6.33±0.20°, 10.62±0.20°, 12.57±0.20°, 13.11±0.20°, 17.85±0.20°, 18.51±0.20°, and 20.99±0.20°.

3. The crystal form according to claim 1, wherein the X-ray powder diffraction pattern has characteristic diffraction peaks at the following angles of 2θ:3.30±0.20°, 6.33±0.20°, 6.55±0.20°, 10.62±0.20°, 12.57±0.20°, 13.11±0.20°, 14.20±0.20°, 16.37±0.20°, 17.85±0.20°, 18.51±0.20°, 19.56±0.20°, 20.99±0.20°, 25.53±0.20°, and 26.35±0.20°.

4. The crystal form according to claim 3, wherein the X-ray powder diffraction pattern having characteristic diffraction peaks at the following angles of 2θ:3.30°, 6.33°, 6.55°, 10.62°, 12.57°, 13.11°, 14.20°, 16.37°, 17.85°, 18.51°, 19.56°, 20.99°, 25.53°, and 26.35°.

5. The crystal form according to claim 4, wherein:

the crystal form is crystal form A, and analysis data of the X-ray powder diffraction pattern is listed below:

| No. | angles of 2θ (°) | Interplanar distance (Å) | Intensity (count) | Relative intensity (%) |
|---|---|---|---|---|
| 1 | 3.30 | 26.76 | 348.60 | 43.99 |
| 2 | 6.33 | 13.95 | 779.58 | 98.38 |
| 3 | 6.55 | 13.50 | 475.77 | 60.04 |
| 4 | 10.62 | 8.33 | 562.38 | 70.97 |
| 5 | 12.57 | 7.04 | 226.50 | 28.58 |
| 6 | 13.11 | 6.76 | 792.44 | 100.00 |
| 7 | 14.20 | 6.24 | 122.94 | 15.51 |
| 8 | 16.37 | 5.42 | 178.19 | 22.49 |
| 9 | 17.85 | 4.97 | 228.61 | 28.85 |
| 10 | 18.51 | 4.79 | 198.30 | 25.02 |
| 11 | 19.56 | 4.54 | 192.79 | 24.33 |
| 12 | 20.99 | 4.23 | 232.26 | 29.31 |
| 13 | 25.53 | 3.49 | 170.02 | 21.46 |
| 14 | 26.35 | 3.38 | 149.03 | 18.81. |

6. The crystal form according to claim 1, wherein a differential scanning calorimetry curve of the crystal form has an endothermic peak with an onset at 235.9° C.±3.0° C.

7. The crystal form according to claim 1, wherein a thermogravimetric analysis curve of the crystal form shows a weight loss up to 7.70% at 160.0-3.0° C.

8. A crystal form of a compound of formula (II), (II)

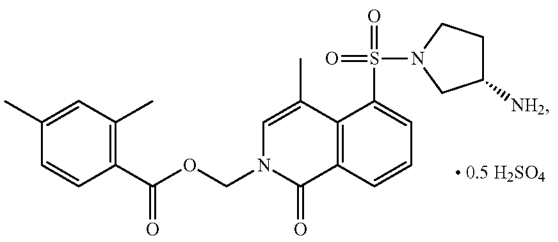

wherein an X-ray powder diffraction pattern has characteristic diffraction peaks at the following angles of 2θ:12.12±0.20°, 16.48±0.20°, 16.95±0.20°, 17.94±0.20°, and 21.87±0.20°.

9. The crystal form according to claim 8, wherein the X-ray powder diffraction pattern has characteristic diffraction peaks at the following angles of 2θ:9.69±0.20°, 12.12±0.20°, 16.48±0.20°, 16.95±0.20°, and 21.87±0.20°.

10. The crystal form according to claim 8, wherein the X-ray powder diffraction pattern has characteristic diffraction peaks at the following angles of 2θ:9.69±0.20°, 12.12±0.20°, 16.48±0.20°, 16.95±0.20°, 17.94±0.20°, 19.23±0.20°, 20.37±0.20°, and 21.87±0.20°.

11. The crystal form according to claim 10, wherein the X-ray powder diffraction pattern has characteristic diffraction peaks at the following angles of 2θ:4.80±0.20°, 9.69±0.20°, 12.12±0.20°, 14.61±0.20°, 16.48±0.20°, 16.95±0.20°, 17.94±0.20°, 19.23±0.20°, 20.37±0.20°, 21.87±0.20°, 27.53±0.20°, 28.72±0.20°, and 33.61±0.20°.

12. The crystal form according to claim 8, wherein a differential scanning calorimetry curve of the crystal form has an endothermic peak with an onset at 239.5±3.0° C.

13. The crystal form according to claim 8, wherein a thermogravimetric analysis curve of the crystal form shows a weight loss up to 1.30% at 200.0±3.0° C.

14. A preparation method for a crystal form B of a compound of formula (II), comprising:

(a) adding a crystal form A of the compound of formula (II) into a solvent to form a suspension; and (b) stirring the suspension at 50° C. for 3 h, filtering, and drying, (II)

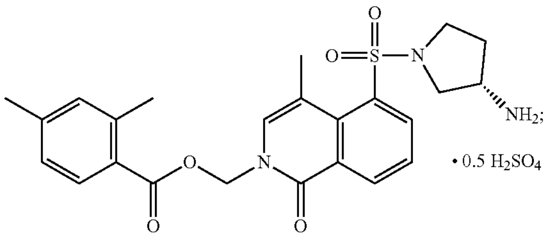

an X-ray powder diffraction pattern of the crystal form A of the compound of formula (II) has characteristic diffraction peaks at the following angles of 2θ: 1.30±0.20°, 6.33±0.20°, 6.55±0.20°, 10.62±0.20°, 12.57±0.20°, and 13.11±0.20°;

an X-ray powder diffraction pattern of the crystal form B of the compound of formula (II) has characteristic diffraction peaks at the following angles of 2θ: 9.12±0.20°, 16.48±0.20°, 16.95±0.20°, 17.94±0.20°, and 21.87±0.20°;

wherein the solvent is selected from the group consisting of isopropanol, tetrahydrofuran, acetonitrile, 2-butanone, and ethyl acetate.

15. A method for treating glaucoma or ocular hypertension, comprising:

administrating the compound according to claim 1 to a subject in need thereof.

16. A method for treating glaucoma or ocular hypertension, comprising:

administrating the compound according to claim 8 to a subject in need thereof.

* * * * *